United States Patent [19]
Kawakita et al.

[11] Patent Number: 5,856,444
[45] Date of Patent: Jan. 5, 1999

[54] THROMBOCYTOPOIESIS STIMULATING FACTOR

[75] Inventors: Makoto Kawakita; Hiromitsu Matsuzaki, both of Kumamoto; Kiyoshi Takatsuki, Kyoto; Kazushi Shibuya, Tokyo; Masato Higuchi, Shizuoka, all of Japan

[73] Assignee: Chugai Seiyaku Kabushiki Kaisha, Tokyo, Japan

[21] Appl. No.: 849,073

[22] PCT Filed: Nov. 30, 1995

[86] PCT No.: PCT/JP95/04226

§ 371 Date: Jul. 18, 1997

§ 102(e) Date: Jul. 18, 1997

[87] PCT Pub. No.: WO96/16987

PCT Pub. Date: Jun. 6, 1997

[30] Foreign Application Priority Data

Nov. 30, 1994 [JP] Japan ..................................... 6-321619
Nov. 8, 1995 [JP] Japan ..................................... 7-316077

[51] Int. Cl.⁶ ..................................................... C07K 1/18
[52] U.S. Cl. .......................... 530/350; 530/351; 424/85.1
[58] Field of Search ..................................... 530/350, 351; 424/85.1

[56] References Cited

FOREIGN PATENT DOCUMENTS 4178400  6/1992  Japan .

OTHER PUBLICATIONS

Fujimoto et al., Biochem. Biophy. Res. Comm., vol. 174(3), pp. 1163–1168, 1991.

Yoshida et al., Cancer Res., vol. 52, pp. 464–469, 1992.

*Primary Examiner*—Chhaya D. Sayala
*Attorney, Agent, or Firm*—Oblon, Spivak, McClelland, Maier & Neustadt, P.C.

[57] ABSTRACT

An object of the present invention is to provide a physiologically active substance having activity in acting on the megakaryocyte-platelet system, in promoting the differentiation and maturation of megakaryocytes, and in promoting the formation of platelets. The present invention relates to a thrombocytopoiesis stimulating factor, characterized in having the following amino acid sequence in its molecule, and to a medicinal composition for treating thrombocytopenia, characterized in containing thrombocytopoiesis stimulating factor as an active component: Xaa Gly Asn Asn Asp Glu Ser Asn Ile Ser Phe Lys Glu Lys Asp Ile (where Xaa indicates that the amino acid is unspecified). The physiologically active substance is useful as an active component or the like in therapeutics and preventives for thrombocytopenia and thrombocytopenic purpura associated with chemotherapy and marrow grafts, and for various other diseases which are prone to bleeding attributed to thrombocytopenia.

2 Claims, 7 Drawing Sheets

THROMBOCYTOPOIESIS STIMULATING FACTOR

TECHNICAL FIELD

The present invention relates to a novel physiologically active substance (thrombocytopoiesis stimulating factor) having activity in acting on cells in the megakaryocyte system, in promoting their differentiation and maturation, and in promoting the formation of platelets, as well as to a medicinal composition containing this physiologically active substance as an active component for the treatment of thrombocytopenia. Since the physiologically active substance (thrombocytopoiesis stimulating factor) of the present invention has activity in acting on the megakaryocyte-platelet system, in promoting differentiation and maturation therein, and in promoting the formation of platelets, it is particularly useful in the medical field as an active component or the like in therapeutics and preventives for thrombocytopenia and thrombocytopenic purpura associated with chemotherapy and marrow grafts, and for various other diseases which are prone to bleeding attributed to thrombocytopenia.

BACKGROUND ART

Blood cells such as erythrocytes, leukocytes, lymphocytes, and platelets are present as material components in the blood, which is an indispensable medium for the somatic cells constituting the body, and these blood cells each have an inherent function in the continual maintenance of the body. Understanding the phenomenon of the differentiation, maturation, proliferation, and the like of these blood cells in the body has long been the subject of research in the field of hematology, but the differentiation and maturation of various blood cells from one type of multifunctional hematopoietic stem cell in the marrow, the roles played by various endogenous humoral factors during the process of differentiation and maturation, and, other facts have recently been elucidated.

In light of such facts, these endogenous humoral factors hold promise as medicinal products such as drugs for the treatment of diseases associated with decreases in the blood cells of the blood cell systems, and a variety of humoral factors, such as erythropoietin, G-CSF, GM-CSF, M-CSF, and interleukin, have thus far been discovered, some of which have been put to actual use as drugs having action in promoting the differentiation and maturation of blood cells such as those in the erythrocyte, leukocyte, and lymphocyte systems.

Platelets, however, are anucleate cells with a diameter of 2 to 3 $\mu$m in the blood, and although they are a type of material component in the blood that plays an important role in hemostatis or thrombogenesis in the body, it has become clear that platelets are formed as a result of the fragmentation of the cytoplasm of megakaryocytes which have matured following the transition from multifunctional hematopoietic cells in the marrow to megakaryoblasts by way of megakaryocyte precursor cells.

There have recently been various reports on the results of research on the megakaryocyte-platelet system. For example, it has been reported that IL-6 has action in promoting the maturation of megakaryocytes, which are precursor cells of platelets (Toshiyuki Ishibashi, et al., Proc. Natl. Acad. Sci. USA., Vol. 86, pp. 5953–5957 (1989), and Toshiyuki Ishibashi, et al., Blood., Vol. 74, pp. 1241–1244 (1989)).

Based on research thus far undertaken, two factors having different types of action are believed to exist in the formation of megakaryocyte colonies from bone marrow cells (N. Williams, et al., J. Cell Physiol., 110, 101 (1982)). Specific examples of such factors which have been reported include megakaryocyte colony stimulating factor (Meg-CSF) which forms megakaryocyte colonies on its own, and megakaryocyte potentiator factor (Meg-POT) which has no activity in forming megakaryocyte colonies in itself but does have activity in increasing megakaryocyte colonies in the presence of Meg-CSF and in promoting their maturation.

Examples that have been reported as having Meg-CSF activity in humans include IL-3 (M. Teramura, et al., Exp. Hematol., 16, 843 (1988)), granulocyte-macrophage colony stimulating factor (M. Teramura, et al., Exp. Hematol., 17, 1011 (1989)), and c-Mpl ligand (F. J. de Sauvage, et al., Nature, 369, 533 (1994), and K. Kaushansky, et al., Nature, 369, 568 (1994)). Examples that have been reported as having Meg-POT activity include IL-6 (M. Teramura and H. Mizoguchi, Int. J. Cell Cloning, 8, 245 (1990)), IL-11 (M. Teramura, et al., Blood, 79, 327 (1992)), and erythropoietin (E. Bruno, et al., Blood, 73, 671 (1989)).

Most of these factors, however, do not have action specific to the megakaryocyte-platelet system. Their activity is known to be expressed as a result of their action on other blood cell systems and on cells other than those of the blood cell systems. As such, even if these were to be administered as medicines in anticipation of their action on the megakaryocyte-platelet system, there is the danger that activity other than the foregoing activity might also be expressed. That is, the aforementioned IL-6, for example, has various other types of action in addition to the aforementioned action, one example of which is that it is known to play a significant role in provoking inflammation as an endogenous acute phase protein, thus suggesting that the use of IL-6 as a medicine might run the risk of serious side-effects.

In light of this, it is important to discover, among factors having action on the megakaryocyte-platelet system, a physiologically active substance that has specific action on said megakaryocyte-platelet system and that is highly active in promoting differentiation and maturation therein, and there is currently a strong need to develop such a physiologically active substance in the relevant fields.

SUMMARY OF THE INVENTION

An object of the present invention is to provide a physiologically active substance having activity in acting on the megakaryocyte-platelet system, in promoting the differentiation and maturation of megakaryocytes, and in promoting the formation of platelets.

The present invention relates to a thrombocytopoiesis stimulating factor, characterized in containing the following amino acid sequence in its molecule, and to a medicinal composition for treating thrombocytopenia, characterized in containing said thrombocytopoiesis stimulating factor as an active component:

Xaa Gly Asn Asn Asp Glu Ser Asn Ile Ser Phe Lys Glu Lys Asp Ile (where Xaa indicates that the amino acid is unspecified).

The aforementioned physiologically active substance is useful as an active component or the like in therapeutics and preventives for thrombocytopenia and thrombocytopenic purpura associated with chemotherapy and marrow grafts, and for various other diseases which are prone to bleeding attributed to thrombocytopenia.

DISCLOSURE OF THE INVENTION

As a result of extensive, painstaking research undertaken in light of the foregoing to find a novel physiologically active substance that would have activity in acting on the megakaryocyte-platelet system, in promoting differentiation, maturation, and/or proliferation therein, and in promoting the formation of platelets, the inventors discovered the presence of a substance having such activity in culture supernatant of the undifferentiated thyroid cancer-derived KHM-5M cell line, the HUT78 cell line from patients suffering from Sezary syndrome, and the like, and they perfected the present invention by successfully extracting, purifying, isolating, and characterizing the target physiologically active substance from said culture supernatant using its activity on the megakaryocyte-platelet system as an index.

An object of the present invention is to provide a novel physiologically active substance (thrombocytopoiesis stimulating factor) having activity in acting on the megakaryocyte-platelet system, in promoting differentiation and maturation therein, and in promoting the formation of platelets.

Another object of the present invention is to provide a novel physiologically active substance (thrombocytopoiesis stimulating factor) having activity in acting on the megakaryocyte-platelet system and in promoting the production of acetylcholinesterase.

Yet another object of the present invention is to provide a medicinal composition for the treatment of thrombocytopenia, characterized in containing said physiologically active substance (thrombocytopoiesis stimulating factor) as an active component.

Still another object of the present invention is to provide an effective medicinal composition for the treatment, prevention, and the like of diseases associated with thrombocytopenia or diseases associated with platelet dysfunction, said medicinal composition being characterized in containing said physiologically active substance as an active component.

The present invention achieving these objectives comprises the following technical means 1. and 2.

1. Thrombocytopoiesis stimulating factor, characterized in having the following characteristics:
   (1) activity in acting on cells of the megakaryocyte system in rodents, and in promoting the production of acetylcholinesterase;
   (2) in vitro activity in promoting the differentiation and maturation of megakaryocytes;
   (3) a molecular weight of about 42 kD, as determined by SDS-PAGE; and
   (4) containing the following amino acid sequence in its molecule:
   Xaa Gly Asn Asn Asp Glu Ser Asn Ile Ser Phe Lys Glu Lys Asp Ile
      (where Xaa indicates that the amino acid is unspecified).
2. A medicinal composition for the treatment of thrombocytopenia, characterized in containing the thrombocytopoiesis stimulating factor defined in 1. above as an active component.

The contents of the present invention are described in detail below.

The novel physiologically active substance (thrombocytopoiesis stimulating factor) pertaining to the present invention is characterized in having activity in acting on the megakaryocyte-platelet system of rodents, and in promoting the production of acetylcholinesterase (sometimes abbreviated as AchE below). However, since this acetylcholinesterase is an enzyme produced during the differentiation and/or maturation of cells in the megakaryocyte system of rodents, the aforementioned activity in promoting the production of AchE indicates that the physiologically active substance pertaining to the present invention would have action on the megakaryocyte-platelet system.

Although the physiologically active substance pertaining to the present invention thus has action on the megakaryocyte-platelet system, the action on the megakaryocyte-platelet system referred to here means having activity in promoting the differentiation and maturation of megakaryocytes or their precursor cells, or in promoting the formation of platelets during the formation of platelets from megakaryocytes.

A preferred method for assaying the aforementioned activity of the physiologically active substance pertaining to the present invention on the megakaryocyte-platelet system is to allow a test substance (sample) to act on bone marrow cells or cells of the megakaryocyte system so as to measure the emergence of enzymes or proteins specific to megakaryocytes or platelets.

Since acetylcholinesterase is produced during the differentiation and maturation of cells of the megakaryocyte system in rodents, the number of cells producing AchE can be counted by staining the cells, for example, or the AchE activity that is produced can be assayed with a spectrophotometer (see Toshiro Nagasawa, et al., Nihon Ketsueki Gakkai Zasshi, 49, pp. 1688–1695 (1986)), or the like, so as to assay the aforementioned activity of the physiologically active substance on the megakaryocyte-platelet system.

As noted below, assay of the activity of the physiologically active substance pertaining to the present invention by these methods of measurement revealed that it had activity in acting on the cells of the megakaryocyte system and in promoting the production of acetylcholinesterase, and that it had activity in promoting differentiation and maturation, and in promoting the formation of platelets.

The physiologically active substance pertaining to the present invention is also characterized by having a molecular weight of about 42 kD, as determined by SDS-PAGE (SDS-polyacrylamide gel electrophoresis). The molecular weight of the physiologically active substance is generally determined by a method for determining molecular weight such as gel filtration or SDS-PAGE; the measured value sometimes varies slightly, depending on the type of measuring method, the type of support or molecular weight marker used in the measurement, the measuring conditions, and the like, but the molecular weight of the physiologically active substance pertaining to the present invention is about 42 kD, as stated above, when determined by SDS-PAGE.

In this case, as described below, the weight can be determined using the 14.4 kD, 20.1 kD, 30 kD, 43 kD, 67 kD, and 94 kD molecular weight markers in the Pharmacia LMW Kit E (by Pharmacia) as molecular weight markers.

The physiologically active substance pertaining to the present invention is also characterized by having the following amino acid sequence in its molecule. As described below, this amino acid sequence was experimentally identified with a protein sequencer.
(sequence)
   Xaa Gly Asn Asn Asp Glu Ser Asn Ile Ser Phe Lys Glu Lys Asp Ile
      (where Xaa indicates that the amino acid is unspecified).

Although the aforementioned undifferentiated thyroid cancer-derived KHM-5M cell line, the HUT78 cell line derived from patients suffering from Sezary syndrome, and the like were given above as examples of desirable sources of the physiologically active substance pertaining to the present invention, the sources are not limited to these. Other examples include the culture supernatant of human-derived cells which can produce the physiologically active substance pertaining to the present invention, those obtained form human bodily fluids such as urine, and those that have been produced by genetic engineering using genes for the physiologically active substance pertaining to the present invention.

As described below in the detailed description of the present invention, the KHM-5M cell line and the HUT78 cell line are used, and those obtained from the culture supernatant of the KHM-5M cell line and HUT78 cell line are given as desirable examples.

A method for preparing the physiologically active substance pertaining to the present invention is described below. The physiologically active substance pertaining to the present invention can be efficiently manufactured by the following steps, for example.

(1) The KHM-5M cell line or the like is cultured.
(2) The culture supernatant of the KHM-5M cell line or the like is recovered.
(3) The culture supernatant is concentrated using an ultrafiltration membrane.
(4) It is purified by the following ((1)) through ((5)):
   ((1)) DEAE-Sepharose FF ion exchange chromatography;
   ((2)) a first run of reverse phase high performance liquid chromatography;
   ((3)) a second run of reverse phase high performance liquid chromatography;
   ((4)) gel filtration; and
   ((5)) SDS-PAGE.

In the present invention, a manufacturing method based on these steps is a desirable example, but the invention is not limited to this. A manufacturing method in which other steps have been added as needed to these steps may be used if desired.

The aforementioned steps are described below.

The step for culturing the KHM-5M cell line or the like in section (1) above can be implemented as desired under culturing conditions allowing said cells to proliferate. That is, the cells can be cultured at 37° C. using medium containing serum or growth factors, such as fetal calf serum or insulin, in a concentration suitable for growing the KHM-5M cells or the like. Examples of suitable media include commonly used media such as DMEM (Dulbecco's Modified Eagle's Medium), IMDM (Iscove's Modified Dulbecco's Medium), and RPMI-1640. The cells should be cultured under conditions that are suitable for growth and then transferred for culture under conditions suitable for recovering the physiologically active substance pertaining to the present invention, such as to a completely synthetic medium containing no serum or the like.

The cells can then be cultured using animal. That is, the cells can be implanted in individual animals, or they can be cultured using animal bodily fluids in individual animals or in diffusion chambers attached to the exterior of individuals. The cells thus cultured using individual animals can then be removed from the individual animals and dispersed for culture in suitable growth medium. Any animals in which the cells can be grown may be used when the cells are cultured using individual animals, desirable examples of which include mice, rats, hamsters, nude mice, nude rats, and the like which have undergone thymectomy or have been treated with anti-thymus antibodies.

In the step for recovering the culture supernatant of the KHM-5M cell line or the like in section (2) above, the culture supernatant should be recovered, for example, by a suitable means from the medium in which the KHM-5M cell line or the like has been cultured in section (1) above. The medium should be removed from the culture vessel following the culture of the KHM-5M cell line or the like, and the cells in the medium and the culture supernatant should be separated as needed by a means such as centrifugation or filtration to recover the culture supernatant.

When the culture supernatant is the culture supernatant of the KHM-5M cell line or the like containing the physiologically active substance pertaining to the present invention, it may be medium containing serum or the like, or it may be the bodily fluid of an animal.

The culture supernatant should be concentrated with an ultrafiltration membrane in section (3) above using a commercially available ultrafiltration membrane by a common method, so as to concentrate the supernatant to a suitable level and thus prepare a liquid concentrate, although the means is not limited to this.

Although the aforementioned KHM-5M cell line, HUT78 cell line, and the like are used as desirable examples of liquid concentrates containing the physiologically active substance pertaining to the present invention, other concentrates such as tissue and cell culture supernatant capable of producing the physiologically active substance pertaining to the present invention, medium in which cells or microbes capable of producing the physiologically active substance pertaining to the present invention have been cultured, or liquids containing the physiologically active substance pertaining to the present invention, can also be used as desired.

Examples of suitable methods which should be selected to purify the physiologically active substance pertaining to the present invention from the concentrate of culture supernatant thus obtained include, but are not limited to, salting out, ultrafiltration, isoelectric precipitation, gel filtration, ion exchange chromatography, hydrophobic chromatography, antibody affinity chromatography, chromatofocusing, absorption chromatography, and reverse phase chromatography, most of which are noted in the literature, such as in Seikagaku Jikken Koza 1: Tanpakushitsu no Kagaku [A First Course in Biochemical Experiments: Protein Science], edited by Nihon Seikagakkai, Tokyo Kagaku Dojin (1976), although the preferred purification steps in the aforementioned step (4) are a combination of ((1)) DEAE-Sepharose FF ion exchange chromatography, ((2)) and ((3)) reverse phase high performance liquid chromatography, ((4)) gel filtration, and ((5)) SDS-PAGE. The physiologically active substance pertaining to the present invention can be efficiently purified by these purification steps.

In step (4) above, DEAE-Sepharose FF ion exchange chromatography is suitable for the ion exchange chromatography, Vydac Protein C4 RP-HPLC is suitable for the reverse phase high performance liquid chromatography, and TSK G3000 SWXL GPC is suitable for the gel filtration.

The physiologically active substance (thrombocytopoiesis stimulating factor) pertaining to the present invention may be thus purified, but once it has been extracted, purified, and characterized, a method suitable for use in isolating and purifying proteins based on these characteristics as indices can be adopted.

The physiologically active substance pertaining to the present invention can also be manufactured by genetic engineering methods. For example, mRNA can be isolated by a common method from the aforementioned established cell line KHM-5M or the like, and the mRNA can be used to prepare a cDNA library by a common method. DNA probes for screening the cDNA library can be designed on the basis of partial amino acid sequences elucidated by the present invention, for example. Alternatively, the physiologically active substance pertaining to the present invention can be enzymatically or chemically cleaved, the fragments can be sequenced, and DNA probes can then be designed based on the resulting amino acid sequences.

The cDNA coding for the physiologically active substance thus obtained can then be inserted into a suitable expression vector, a host can transformed with the expression vector, and the transformants can be cultured so as to manufacture the physiologically active substance pertaining to the present invention. Common hosts, including prokaryote cells such as E. coli, lower eukaryote cells such as yeast, and higher eukaryote cells such as mammalian cells, should be used as the host.

The characteristics of the physiologically active substance (thrombocytopoiesis stimulating factor) pertaining to the present invention manufactured by the aforementioned steps are given below.

(1) Molecular Weight

The physiologically active substance pertaining to the present invention has a molecular weight of about 42 kD, as determined by SDS-PAGE.

(2) Partial Amino Acid Sequence

The physiologically active substance pertaining to the present invention has the following amino acid sequence in its molecule:

Xaa Gly Asn Asn Asp Glu Ser Asn Ile Ser Phe Lys Glu Lys Asp Ile (where Xaa indicates that the amino acid is unspecified).

(3) Thrombocytopoiesis Stimulating Activity ((1)) The substance has activity in acting on the cells of the megakaryocyte system in rodents and in promoting the production of acetylcholinesterase.

((2)) The substance has in vitro activity in promoting the differentiation and maturation of megakaryocytes.

The aforementioned undifferentiated thyroid cancer-derived KHM-5M cell line screened and established as a cell line by the inventors was deposited on Nov. 29, 1994 as KHM-5M with the accession number FERM BP-4901 at the National Institute of Bioscience and Human-Technology under the Agency of Industrial Science and Technology, a public microorganism depositary authority in Japan, at 1–3, Higashi 1'-Chome, Tsukubashi, Ibaraki-ken, Japan (Postal code number 305) (international deposit based on the Budapest Treaty). As indicated in Example 2 described below, the aforementioned KHM-5M was deposited as a mycoplasma-decontaminated KHM-5M cell line pursuant to notification by the international depositary authority.

The medicinal composition for the treatment of thrombocytopenia in the present invention is described below.

The medicinal composition pertaining to the present invention is characterized in containing the physiologically active substance (thrombocytopoiesis stimulating factor) pertaining to the present invention as an active component. A physiologically active substance (thrombocytopoiesis stimulating factor) having the aforementioned amino acid sequence at the N terminal or a suitable site in the molecule can be used. The medicinal composition pertaining to the present invention can be obtained simply by treating the physiologically active substance (thrombocytopoiesis stimulating factor) pertaining to the present invention by a pharmaceutically necessary step such as lyophilization or disinfecting sterilization to produce adequate effects, but it can, of course, also be formulated by a common method by adding pharmaceutically permissible adjuvants as desired to the physiologically active substance.

Examples of such adjuvants include bases, stabilizers, antiseptics, preservatives, emulsifiers, suspension agents, solubilizers, dissolving adjuvants, lubricants, flavorings, colorants, perfumes, soothing agents, excipients, binders, thickeners, buffers, and the like. Specific examples include calcium carbonate, lactose, sucrose, sorbitol, mannitol, starch, amylopectin, cellulose derivatives, gelatin, cacao butter, injection distilled water, sodium chloride aqueous solution, Ringer's solution, glucose solution, and human serum albumin (HSA).

When these adjuvants are used to prepare the medicinal composition pertaining to the present invention, suitable adjuvants should be selected for use as in, for example, drug additive charts (published by Tokyo Iyakuhin Kogyo Kyokai Iji Hoki I-inkai and by Osaka Iyakuhin Kogyo Kyokai Iji Hoki Kenkyu I-inkai). The amount of adjuvant that is used should be suitably selected according to the pharmaceutical configuration and the like of the medicinal composition within a pharmaceutically permissible range.

The dosage of the medicinal composition pertaining to the present invention is suitably selected depending on patient condition, age, gender, weight, and the like. The method of administration is suitably selected, depending on patient condition, from among various methods of administration such as oral administration, intramuscular administration, intraperitoneal administration, intradermal administration, subcutaneous administration, intravenous administration, intra-arterial administration, and rectal administration.

The medicinal composition is useful as a therapeutic, preventive, or the like for thrombocytopenia and thrombocytopenic purpura associated with chemotherapy and marrow grafts, for various other diseases which are prone to bleeding attributed to thrombocytopenia, and for diseases associated with megakaryocyte and/or platelet dysfunction.

BEST MODE FOR CARRYING OUT THE INVENTION

The present invention is described in detail below with reference to examples, but the present invention is not limited to these. Abbreviations commonly used in the field are sometimes used in the following description.

EXAMPLE 1

(1) Subculture of Human-Derived KHM-5M Cell Line

The human-derived KHM-5M cell line is an established line derived from patients of undifferentiated thyroid cancer. This cell line was subcultured by the following method.

First, 100 mL of RPMI-1640 medium containing 10% immobilized fetal calf serum (FCS) was inoculated with the human-derived KHM-5M the. cell line for three days of culture at 37° C. in culture flasks with a bottom surface area of 175 cm² (by Falcon).

Following the conclusion of culture, the medium was removed from the flasks and the cells were washed twice with RPMI-1640, approximately 2 to 5 mL of trypsin solution containing EDTA was then added to the flasks to separate the cells, and then RPMI-1640 medium containing 10% FCS was added to them to prepare a cell suspension, which was cultured at 37° C. in culture flasks.

Subsequent subculture was performed in the same manner.

(2) Culture of KHM-5M Cell Line and Preparation of Culture Supernatant

The KHM-5M cell line was cultured for 3 days at 37° C. 5% $CO_2$ and 100% humidity in culture flasks having a floor surface area of 175 cm² containing 100 mL RPMI-1640 medium containing 10% immobilized fetal calf serum. Following the conclusion of culture, the medium was removed from the flasks, and the cells were washed three times with IMDM medium and cultured for another 3 days in culture flasks containing 100 mL IMDM medium. The obtained culture supernatant was collected and centrifuged for 20 minutes at 8000 rpm, and the resulting supernatant was used as KHM-5M cell line culture supernatant and stored frozen at −20° C.

(3) Purification of Physiologically Active Substance (Thrombocytopoiesis Stimulating Factor) in Present Invention.

1) Concentration by Ultrafiltration Membrane

About 20 L of the aforementioned culture supernatant was thawed at room temperature and concentrated to between 500 and 1000 mL by an ultrafiltration membrane (PAN 1200 by Asahi Medical, and PM-10 by Amicon), and the concentrate was stored frozen.

2) DEAE-Sepharose FF Ion Exchange Chromatography.

The aforementioned concentrated culture supernatant was dialyzed against 20 mM Tris hydrochloric acid buffer (pH 7.4). This was adsorbed to a DEAE-Sepharose FF (by Pharmacia) column equilibrated with the same buffer, and was eluted with the NaCl concentration increased step by step (250 mM and 1000 mM). The fraction eluted with 250 mM NaCl was purified in the following manner.

3) Vydac Protein C4 RP-HPLC

Figure 1:
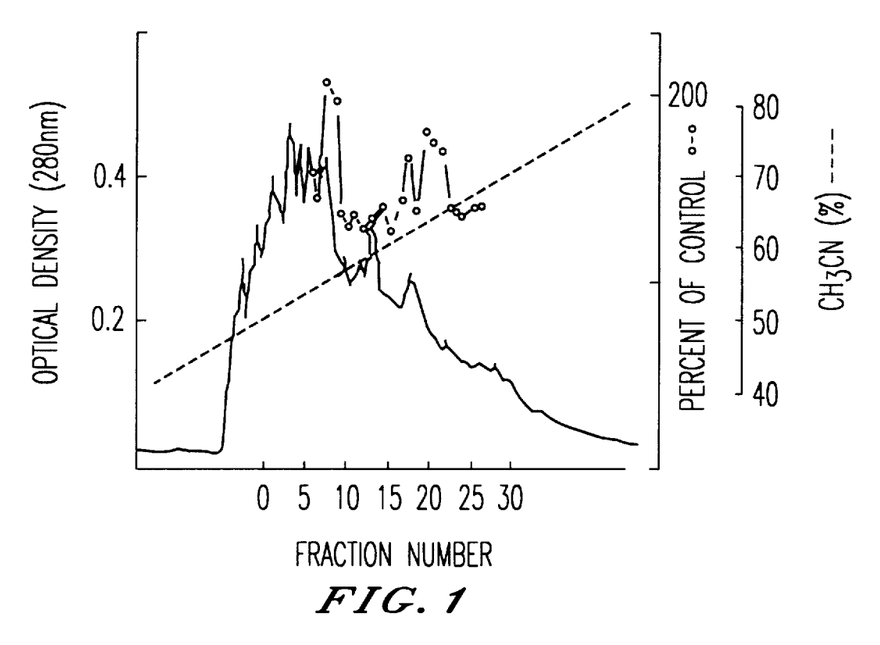
FIG. 1 is a monitoring chart for reverse phase high performance liquid chromatography in Example 1 of the present invention.

The fraction eluted with the aforementioned 250 mM NaCl was fractionated by reverse phase high performance liquid chromatography using a Vydac Protein C4 (by Vydac) column. That is, it was adsorbed at a flow rate of 8 mL/min to a column equilibrated with 0.1% trifluoroacetic acid solution containing 40% acetonitrile, and was eluted with the concentration of the acetonitrile increased linearly to 80% over 60 minutes. FIG. 1 shows the elution pattern by the high performance liquid chromatography. Assay of the activity of the resulting fractions revealed activity in Fraction Nos. 19 through 21.

4) 2nd Vydac Protein C4 RP-HPLC

Figure 2:
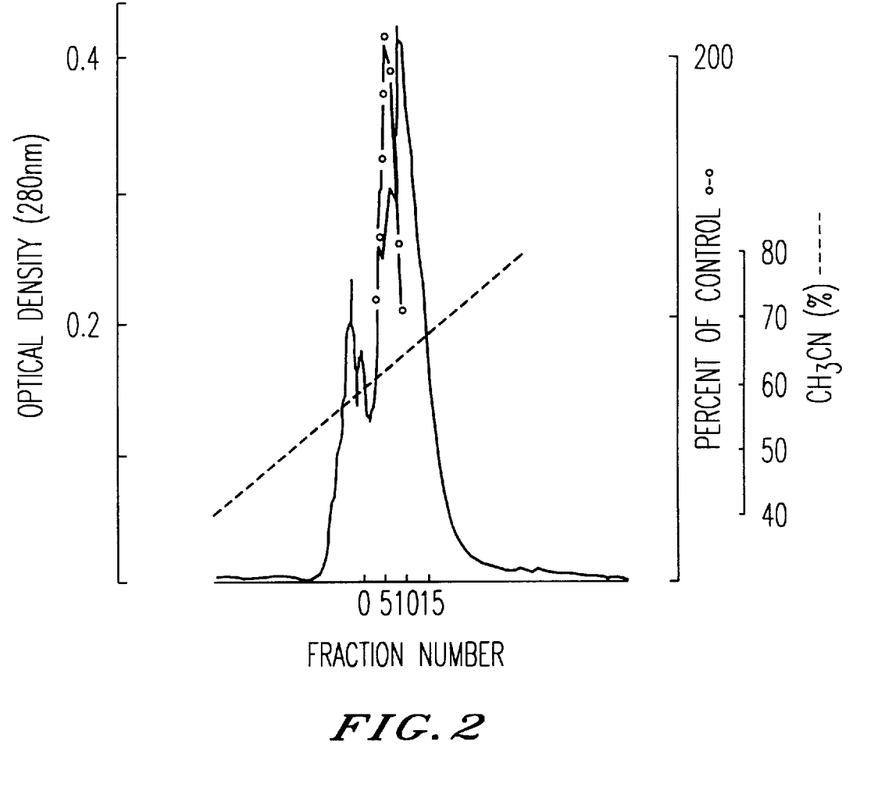
FIG. 2 is a monitoring chart for a second run of reverse phase high performance liquid chromatography in Example 1 of the present invention.

The aforementioned active fractions were again fractionated by reverse phase high performance liquid chromatography using a second Vydac Protein C4 (by Vydac) column. That is, the fractions were adsorbed at a flow rate of 1 mL/min to a column equilibrated with 0.1% trifluoroacetic acid solution containing 40% acetonitrile, and were eluted with the concentration of the acetonitrile increased linearly to 80% over 40 minutes. FIG. 2 shows the elution pattern from the second high performance liquid chromatography. Assay of the activity of the resulting fractions revealed activity in Fraction Nos. 7 through 9.

5) TSK G3000 SWXL GPC

Figure 3:
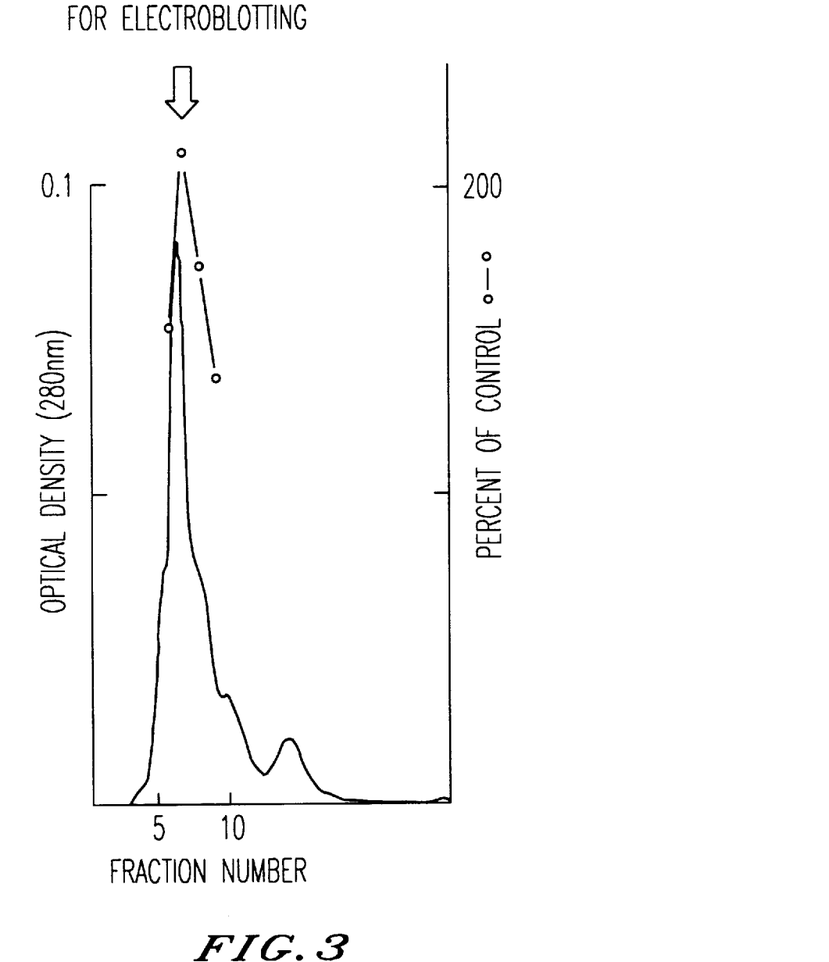
FIG. 3 shows the elution pattern for gel filtration with TSK G3000 SWXL in Example 1 of the present invention.

The aforementioned active fractions were each subjected to-gel filtration using a TSK G3000 SWXL (by Toso) column. The fractions were gel filtrated at a flow rate of 0.25 mL/min on the columns equilibrated with 0.1% trifluoroacetic acid solution containing 40% acetonitrile. Assay of the activity of the resulting fractions revealed activity in all of Fractions No. 6 through 9. FIG. 3 shows an example of the results obtained by fractionating Fraction No. 8 from the 2nd Vydac Protein C4 RP-HPLC in the TSK G3000 SWXL GPC.

6) SDS-PAGE

Assay by SDS-PAGE revealed 42 kD silver staining bands as a correlation with activity in each of the fractions from the aforementioned TSK G3000 SWXL GPC. To confirm that the proteins were active target, the assay by the SDS-PAGE was performed, and was followed by extraction of the proteins from the gel. That is, Fraction No. 6, which was obtained by TSK G3000 SWXL GPC fractionation of Fraction No. 7 from the 2nd Vydac Protein C4 RP-HPLC, was underwent SDS under nonreducing conditions (4% SDS, 20% glycerol, and 0.125M Tris hydrochloric acid buffer (pH 6.8) treated for 3 minutes at 100° C., immediately after which resulting solution mixed with sample in ratio of 1:1), and was electrophoresed at constant current (concentration gel: 10 mA; separation gel: 15 mA) using SDS-PAGE minigel (10 T%, by TEFCO).

Figure 4:
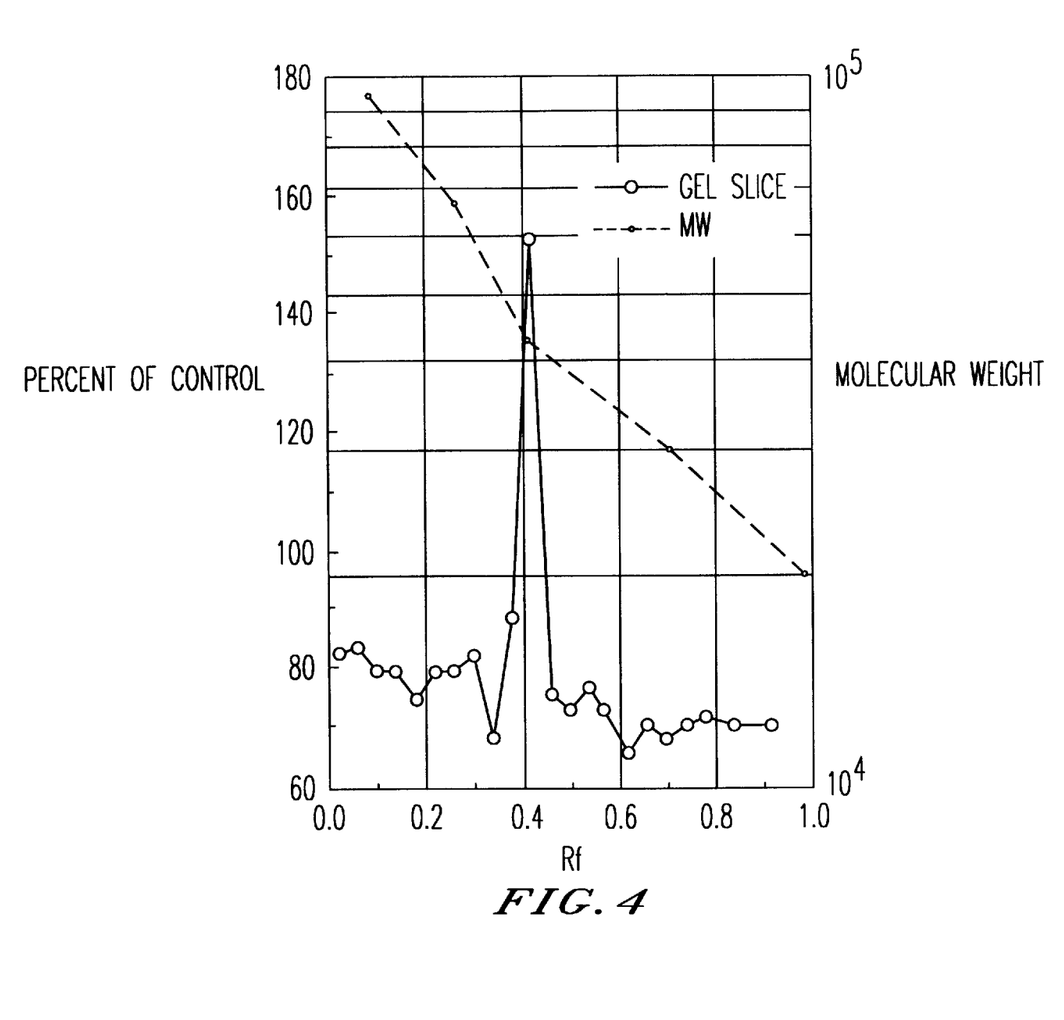
FIG. 4 shows the results obtained by assaying activity of proteins extracted following SDS-PAGE in Example 1 of the present invention.

As molecular weight markers, 14.4 kD, 20.1 kD, 30 kD, 43 kD, 67 kD, and 94 kD molecular weight markers from the LMW Kit E by Pharmacia were used. Following the electrophoresis, the gel was sliced in 2 mm intervals and subjected to IMDM medium (1 mL) containing 0.1% BSA to elute the proteins. The eluted proteins were filtrated with filters having a pore size of 0.2 μm (New Steradisk, by Kurabo) and assayed biological activity. As shown in FIG. 4, activity was found around a molecular weight of 42 kD (42 to 45 kD). The silver staining bands found at a molecular weight of 42 kD were thus considered active.

(4) Assay of Activity (Action on Cells of Megakaryocyte)

1) AchE Assay (Acetylcholinesterase Assay)

((1)) Bone marrow cells were taken from the femur and tibia in C57BL/6Cr mice (6 to 10 weeks old) (by Nihon SLC), and were suspended in 10% FCS/IMDM medium. After removing bone fragments and the like from the suspension through a 100 μm mesh filter, the suspension was subjected to cell culture Petri dishes and incubated for 90 minutes at 37° C. and 5% $CO_2$. Cells adhering to the Petri dishes were removed from the dishes, and KAC2 solution (by Otsuka Assay Kenkyujo) was added in an amount of 1/10 to the nonadherent cell suspension in the dishes, and the cells were incubated for 1 hour at 37° C. while stirred every 10 minutes.

The nonadherent cell suspension was layered at 10 mL per 4 mL lympholyte M solution and centrifuged for 30 minutes at 1500 rpm at 25° C. using a centrifuge.

The nonphagocytic cells existing at the interface between the lympholyte M solution and medium were collected, and the cells were recovered by precipitation with 5 minutes of centrifugation at 2000 rpm. The resulting nonadherent and nonphagocytic cells were washed twice with 0.1% BSA/IMDM medium.

((2)) Assay of Activity

As samples for the assay of activity, the cells were diluted with 0.1% BSA/IMDM. The aforementioned samples and 0.1% BSA/IMDM medium were added as the test groups and control groups, respectively, on the 96-well microplates prepared, in amounts of 100 μL/well. The aforementioned cells for the assay of activity were suspended in an amount of $0.8 \times 10^6$ cells/mL in IMDM medium containing 10% FCS treated with 10% DFP (diisopropyl fluorophosphate), and the suspension was added in an amount of 100 μL/well on the microplates, and incubated for 4 days at 37° C.

Following the conclusion of the culture, 150 μL supernatant was removed from each well after 10 minutes of centrifugation at 1500 rpm of each plate and replaced by 150 μL per well of PBS(−) adjusted to pH 7.2. And then, 3.15 mg/mL DTNB/1% sodium citrate solution was then diluted 10-fold with 1% Triton X-100 solution, the diluted solution was added to the well of each plate in an amount of 50 μL/well and agitated with a plate mixer, and then the difference in absorbance at wavelengths of 405 and 690 nm was determined as the absorbance at 0 minute.

Then, 2.17 mg/mL acetylthiocholine iodide solution was added to the well in an amount of 20 μL/well, and the solution was subjected to incubation about for 30 and 60 minutes at room temperature, and then the difference in absorbance at wavelengths of 405 and 690 nm was measured (absorbance at 30 or 60 min) to determine the Δ OD (difference in absorbance at 30 or 60 min and 0 min). Besides, DTNB is the abbreviation for 5,5'-dithiobis-(2-nitrobenzoic acid).

Cases in which the Δ OD was clearly higher than that in the control group were attributed to acetylcholinesterase activity, which was concluded to indicate action on the hematopoiesis of the platelet system.

((3)) Results

AchE assay was carried out by the aforementioned method using as samples proteins eluted from the gel around 42 kD in (3)6) above. The results of the assay revealed higher acetylcholinesterase activity in the samples than in the control groups.

(5) Amino Acid Sequencing

1) Identification Method

Figure 5:
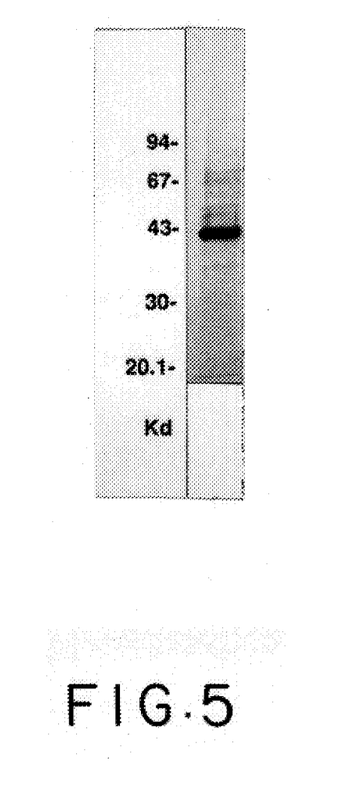
FIG. 5 shows the pattern for protein staining obtained by transfer to PVDF membrane following SDS-PAGE in Example 1 of the present invention.

An active fraction (Fraction No. 8) obtained in the second reverse high performance liquid chromatography (by Vydac) was fractionated by TSK G3000 SWXL gel filtration chromatography (by Toso). SDS was added to a final concentration of 0.04% to Fraction No. 7, which was found to have activity, and the fraction was concentrated under $N_2$ gas blown. The concentrated fraction was neutralized with 0.1N NaOH and was mixed at a ratio of 1:1 with sample treatment solution (4% SDS, 10% 2-mercaptoethanol, 20% glycerol, and 0.125M Tris hydrochloric acid buffer (pH 6.8)) for 3 minutes of treatment at 100° C. The resulting sample was added to SDS-PAGE mini (10 T %, by TEFCO) gel and electrophoresed at constant current (concentration gel: 10 mA; separation gel: 15 mA). Following electrophoresis, it was transferred for 4 hours at 140 mA to PVDF membrane using a semi-dry blotting device (Trans-Blot SD Semi-Dry Transfer Cell, by Bio-Rad) and was then stained with Coomassie Blue dye (FIG. 5) (Hisashi Hirano, Idenshi Kuroningu no tame no Tanpakushitsu Kozo Kaiseki [Protein Structural Analysis for Cloning Genes], pp. 41–71).

The 42 kD band on the membrane was cut out, and subjected to a model 476A protein sequencer (by Applied Biosystems) to determine the amino acid sequence of the N terminal in the molecule. That is, free PTH-amino acids isolated from the molecule through ultraviolet absorption by Edman degradation were detected and the amino acid sequence of it was identified based on the retention time of previously analyzed reference PTH-amino acids (by Applied Biosystems).

2) Results

The results of the identification mentioned above revealed that the physiologically active substance (thrombocytopoiesis stimulating factor) pertaining to the present invention had the following amino acid sequence at the N terminal of its molecule:

Xaa Gly Asn Asn Asp Glu Ser Asn Ile Ser Phe Lys Glu Lys Asp Ile (where Xaa indicates that the amino acid is unspecified).

EXAMPLE 2

(Production Mechanism of Physiologically Active Substance of Present Invention)

The inventors were notified by the National Institute of Bioscience and Human-Technology under the. Agency of Industrial Science and Technology that the deposited KHM-5M cell line was contaminated by mycoplasma. The inventors thus studied the effects of mycoplasma contamination on the production of the physiologically active substance (thrombocytopoiesis stimulating factor) pertaining to the present invention to elucidate the production mechanism of the physiologically active substance pertaining to the present invention.

(1) Method

Methods other than the following were based on the same methods as in Example 1.

1) Subculture of Cell Line, and Preparation of Culture Supernatant

The cell line was subcultured in RPMI-1640 medium (or IMDM medium) containing 10% fetal bovine serum (FBS). Supernatant obtained by culturing the cells in the presence or absence of FBS and removing the cells from the culture by centrifugation was used as sample to ascertain the production of the physiologically active substance.

2) Mycoplasma Infection

The infectious mycoplasma contaminating the cell line was removed from the cells with MC-210 by Dainippon Seiyaku. That is, MC-210 was added to a final concentration of 0.5 μg/mL to RPMI 1640 medium (or IMDM medium) containing 10% fetal bovine serum (FBS) for subculture of the cells from 7 to 14 days. And then, the cells were subcultured several times with medium to which no MC-210 had been added to obtain a cell line from which the mycoplasma had been removed.

3) Preparation of Peptide Antibodies Containing the N Terminal Amino Acid Sequence of the Physiological Active Substance A peptide consisting of 19 amino acids including the N terminal amino acid sequence of the physiologically active substance was synthesized by the MAP method (Sawadi Technology) to make antigen. The MAP peptide was made into an emulsion with Freund's complete adjuvant, and this was then used in the intradermal inoculation of rabbits. The serum of such rabbits was designated anti-Sb serum. Some of the anti-Sb serum was purified with affinity (AF anti-Sb antibodies) using columns on which peptides of the physiologically active substance had been combined.

4) Detection of Physiological Substance

The physiologically active substance was detected by Western blotting using anti-Sb serum or AF anti-Sb antibodies. SDS-PAGE for the substance was carried out by a method modified partially from the method of Laemmli. Samples to be subjected were diluted to suitable concentrations and mixed at a ratio of 1:1 with TEFCO sample buffer for 3 minutes of treatment at 100° C. Molecular weight of the samples was estimated using TEFCO molecular weight markers (by TEFCO) as reference proteins. Electrophoresis of the samples was run at constant current of 18 mA using the Electrophoresis Buffer system by Bio-Rad in TEFCO SDS-PAGE mini (10 T %, 1 mm) gel. Following the conclusion of electrophoresis, the proteins in the gel were transferred to a PVDF membrane using the Bio-Rad Semi-Dry Trans-Blot device. The transfer was effected with 30 minutes of the electrophoresis at a constant voltage of 10 to 20 V in an SDS-added Bjerrum and Schafer-Nielsen transfer buffer system. Proteins were stained with CBB R250 in the reference protein lanes. Anti-Sb serum or AF anti-Sb antibodies were used as primary antibodies and alkali phosphatase-conjugated anti-rabbit IgG antibodies were used as secondary antibodies for immunoenzyme staining in the sample lanes.

5) Detection of Mycoplasma

A Mycoplasma PCR Primer Set (by Stratagene) was used to detect the mycoplasma. Genomic DNA from the cells was prepared with a QIAamp Blood Kit.

6) Preparation of Mycoplasma-Infected Cell Line

The culture supernatant of contaminated HUT78 and other cell lines which were similarly assumed to be contaminated by mycoplasma were used as contaminating mycoplasma. This mycoplasma was added to previously decontaminated HUT78 cell line and the cells were subcultured several times to produce contaminated cell lines.

(2) Test and Results

1) Effects of Mycoplasma Contamination on Production of Physiologically Active Factor in KHM-5M Cell Line As described above, the KHM-5M cell line used in Example 1 was an established cell line derived from patients afflicted with undifferentiated thyroid cancer, and mycoplasma contamination of this KHM-5M was confirmed with a Mycoplasma PCR Primer Set. However, when MC-210 was used to remove the mycoplasma infecting the KHM-5M cell line, the physiologically active substance pertaining to the present invention could not be detected. This suggests the possibility that mycoplasma infection plays a role in the production of the physiologically active factor.

2) Production of Physiologically Active Factor in Various Cell Lines, and Mycoplasma Infection Studies were done to determine whether or not mycoplasma infection played a role in cell lines, other than the KHM-5M cell line, producing the physiologically active substance. Of the cell line culture supernatant studied, HUT78 was the one cell line in which the physiologically active substance could be detected. HUT78 is a T-cell line derived from the peripheral blood of patients afflicted with Sezary syndrome. Mycoplasma infection was also confirmed by the Mycoplasma PCR Primer Set in this cell line. The physiologically active substance could not be detected in the culture supernatant when MC-210 was used to remove the contaminating mycoplasma in the same manner as in the KHM-5M cell line. Although HUT78 can be acquired as a commercially available product (ATCC TIB161), the HUT78 used in Example 2 was contaminated with mycoplasma in some form during subculture.

3) Production of Physiologically Active Factor by Mycoplasma Contamination

The aforementioned results made it clear that, among cell lines producing the physiologically active substance pertaining to the present invention, both undifferentiated thyroid cancer-derived KHM-5M and Sezary syndrome-derived HUT78 were contaminated by mycoplasma. The specific bands could not be detected in Western blotting in either case when the mycoplasma was removed. In light of the above, it was assumed that mycoplasma infection plays a role in the production of the physiologically active substance. Since the physiologically active substance is not produced in other cell lines contaminated with mycoplasma, on the other hand, it was concluded that certain types of mycoplasma or certain types of cell lines play a role. Analysis by Western blotting was then undertaken to determine whether or not the physiologically active substance was produced when mycoplasma-free HUT78 cell lines were contaminated with the mycoplasma contaminating HUT78 or the mycoplasma contaminating other cell lines.

Figure 6:
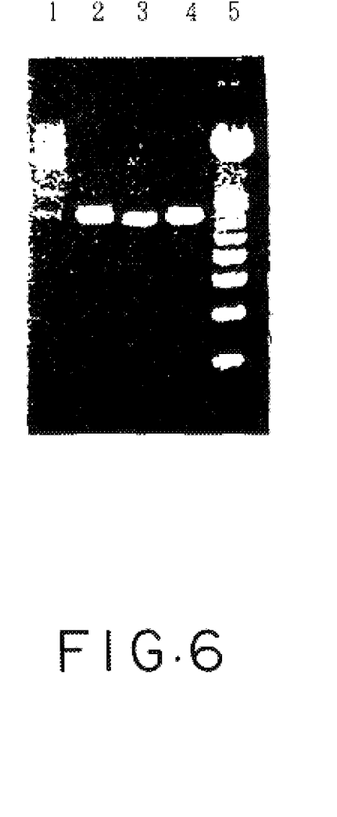
FIG. 6 shows the results obtained when the mycoplasma of various cell lines was detected with a Mycoplasma PCR Primer Set.

The Mycoplasma PCR Primer Set was first used to verify that the cell lines were infected with mycoplasma. The results are given in FIG. 6. In the figure, 1 indicates mycoplasma-decontaminated HUT78, 2 indicates mycoplasma-contaminated HUT78, 3 indicates HUT78 recontaminated with mycoplasma derived from other cell lines, 4 indicates HUT78 recontaminated with HUT78-derived mycoplasma, and 5 indicates a 100 bp Ladder marker (by Pharmacia). Bands specific to mycoplasma were detected by PCR in HUT78 cell lines contaminated with HUT78 cell line-derived mycoplasma and with mycoplasma derived from other cell lines. However, the size of the bands differed, suggesting that they were different types of mycoplasma. The HUT78 cell line-derived mycoplasma showed a migration pattern similar to that of Mycoplasma fermentans.

Figure 7:
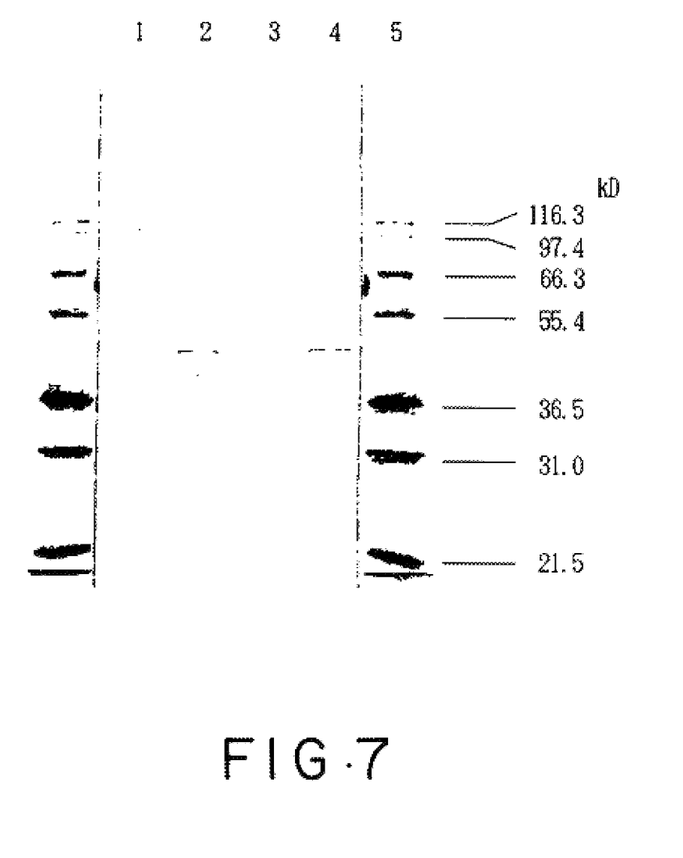
FIG. 7 shows the results obtained when production of the physiologically active substance of the present invention was detected in the culture supernatant of the cell lines by Western blotting.

Analysis by Western blotting of the production of the physiologically active substance in culture supernatant revealed specific bands in the culture supernatant of cells contaminated with HUT78 cell line-derived mycoplasma but none in the supernatant of cells contaminated with mycoplasma derived from other cell lines. The results are given in FIG. 7. In the figure, 1 indicates mycoplasma-decontaminated HUT78, 2 indicates mycoplasma-contaminated HUT78, 3 indicates HUT78 recontaminated with mycoplasma derived from other cell lines, 4 indicates HUT78 recontaminated with HUT78-derived mycoplasma, and 5 indicates a molecular weight marker (by TEFCO). It was thus assumed that contamination by a specific mycoplasma played a role in the production of the physiologically active substance.

INDUSTRIAL APPLICABILITY

The physiologically active substance pertaining to the present invention is a factor having platelet potentiating activity that acts on the megakaryocyte-platelet system, and it has activity in promoting the differentiation and maturation of megakaryocytes and in promoting the formation of platelets. The medicinal composition of the present invention, which contains this physiologically active substance as an active component, is useful as a therapeutic and preventive for thrombocytopenia and thrombocytopenic purpura associated with chemotherapy and marrow grafts, and for various other diseases which are prone to bleeding attributed to thrombocytopenia.

We claim:

1. A thrombocytopoiesis stimulating factor having the following characteristics:

(a) activity on cells of the megakaryocyte system in rodents;

(b) promoting the production of acetylcholinesterase;

(c) in vitro activity in promoting the differentiation and maturation of megakaryocytes;

(d) having a molecular weight of about 42 kD as determined by SDS-PAGE; and (e) containing the following amino acid sequence:
Xaa Gly Asn Asn Asp Glu Ser Asn Ile Ser Phe Lys Glu Lys Asp Ile, wherein Xaa is an unspecified amino acid.

2. A composition for the treatment of thrombocytopenia comprising the thrombocytopoiesis factor of claim 1.

* * * * *

UNITED STATES PATENT AND TRADEMARK OFFICE
CERTIFICATE OF CORRECTION

PATENT NO. : 5,856,444
DATED : January 5, 1999
INVENTOR(S) : Makoto KAWAKITA et al.

It is certified that error appears in the above-identified patent and that said Letters Patent is hereby corrected as shown below:

On the title page, item [86] PCT Number should read:

--PCT No.:  PCT/JP95/002446--

Signed and Sealed this

Twenty-fifth Day of May, 1999

Attest:

Q. TODD DICKINSON

*Attesting Officer*  *Acting Commissioner of Patents and Trademarks*

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
( A ) LENGTH: 16 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Peptide
( B ) LOCATION: 1..16
( D ) OTHER INFORMATION: /product= "Xaa-1 is an unspecified amino acid"
/ note= "Method of Determining Feature: E"

( x i ) SEQUENCE DESCRIPTION: SEQ ID NO:1:

Xaa Gly Asn Asn Asp Glu Ser Asn Ile Ser Phe Lys Glu Lys Asp Ile
1               5                   10                  15